(12) United States Patent
Liu et al.

(10) Patent No.: US 11,039,641 B2
(45) Date of Patent: Jun. 22, 2021

(54) ELECTRONIC CIGARETTE ATOMIZER

(71) Applicant: CHINA TOBACCO HUNAN INDUSTRIAL CO., LTD., Hunan (CN)

(72) Inventors: Jianfu Liu, Hunan (CN); Kejun Zhong, Hunan (CN); Xiaoyi Guo, Hunan (CN); Wei Huang, Hunan (CN); Yuangang Dai, Hunan (CN); Xinqiang Yin, Hunan (CN); Jianhua Yi, Hunan (CN); Hong Yu, Hunan (CN); Yongquan Zhou, Hunan (CN)

(73) Assignee: CHINA TOBACCO HUNAN INDUSTRIAL CO., LTD., Hunan (CN)

( * ) Notice: Subject to any disclaimer, the term of this patent is extended or adjusted under 35 U.S.C. 154(b) by 363 days.

(21) Appl. No.: 16/300,236

(22) PCT Filed: Dec. 15, 2016

(86) PCT No.: PCT/CN2016/110101
§ 371 (c)(1),
(2) Date: Nov. 9, 2018

(87) PCT Pub. No.: WO2017/206480
PCT Pub. Date: Dec. 7, 2017

(65) Prior Publication Data
US 2019/0150519 A1    May 23, 2019

(30) Foreign Application Priority Data
Jun. 3, 2016    (CN) .......................... 201620535446.9

(51) Int. Cl.
*A24F 40/05*    (2020.01)
*A24F 40/00*    (2020.01)
(Continued)

(52) U.S. Cl.
CPC .............. *A24F 40/05* (2020.01); *A24F 40/00* (2020.01); *A24F 40/30* (2020.01); *A24F 40/485* (2020.01);
(Continued)

(58) Field of Classification Search
CPC ...... A24F 47/002; A24F 47/008; A24F 47/00; A24F 40/05; A24F 40/10; A24F 40/20;
(Continued)

(56) References Cited

U.S. PATENT DOCUMENTS

2014/0166029 A1* 6/2014 Weigensberg ........ A24F 47/008
131/329
2016/0089508 A1    3/2016 Smith et al.

FOREIGN PATENT DOCUMENTS

| CN | 103689812 A | 4/2014 |
|---|---|---|
| CN | 204742639 U | * 11/2015 |
| CN | 204742639 U | 11/2015 |
| CN | 105433445 A | 3/2016 |

(Continued)

OTHER PUBLICATIONS

Wu, "CN 204742639, machine translation", published Nov. 11, 2015 (Year: 2015).*

*Primary Examiner* — Alex B Efta
(74) *Attorney, Agent, or Firm* — Mauriel Kapouytian Woods LLP; Liang Huang; Michael Mauriel

(57) ABSTRACT

An electronic cigarette atomizer, including a shell; one end of the shell is in fixed connection with a suction nozzle; an ultrasonic atomization piece is fixed in the shell; the ultrasonic atomization piece is in contact with a liquid guide body; the liquid guide body is communicated with a liquid storage cavity; an atomization outlet of the ultrasonic atomization piece is communicated with an airflow passage; solid perfume are provided on the airflow passage; the solid perfume are in contact with a heating device; and a tail end (Continued)

of the airflow passage is communicated with the suction nozzle. The ultrasonic atomization piece is adopted to atomize the tobacco tar to produce smoke, meanwhile the solid perfume are heated by the heating device to produce fragrance, finally the smoke is mixed with the fragrance, in this case, the mixed smoke has the fragrance of the real cigarette.

15 Claims, 7 Drawing Sheets

(51) Int. Cl.
*A24F 40/30* (2020.01)
*A24F 40/10* (2020.01)
*A24F 40/20* (2020.01)
*A61M 15/00* (2006.01)
*A24F 40/485* (2020.01)

(52) U.S. Cl.
CPC ......... *A61M 15/0085* (2013.01); *A24F 40/10* (2020.01); *A24F 40/20* (2020.01)

(58) Field of Classification Search
CPC ................ B05B 17/06; B05B 17/0607; A61M 15/0085
See application file for complete search history.

(56) References Cited

FOREIGN PATENT DOCUMENTS

| | | | |
|---|---|---|---|
| CN | 105495698 A | 4/2016 |
| CN | 105559251 A | 5/2016 |
| CN | 105795527 A | 7/2016 |
| CN | 205671480 U | 11/2016 |

* cited by examiner

ELECTRONIC CIGARETTE ATOMIZER

CROSS REFERENCE TO RELATED APPLICATIONS

This application is a national phase application of international application number PCT/CN2016/110101 filed on Dec. 15, 2016, which claims priority to Chinese application number 201620535446.9 filed on Jun. 3, 2016. The entire contents of these applications are hereby incorporated herein by reference.

TECHNICAL FIELD

The present invention relates to an electronic cigarette atomizer.

BACKGROUND ART

The taste of the existing electronic cigarette is greatly different from that of the cigarette on the market, thereby affecting the popularization and promotion of the electronic cigarette; the current common solution is to heat and atomize tobacco tar by using heating wires to produce smoke by the tobacco tar, but the taste of the smoke has too much difference with that of the real cigarette, thereby failing to meet the demands of users; meanwhile the heating wires in the electronic cigarette require high power to atomize the tobacco tar into the smoke, thereby being likely to produce burnt flavor in an atomization process, resulting in the problem that the smoking taste becomes worse, moreover the structure is complicated, and the tobacco tar leaks easily; and thus, in order to meet the market demands, it is necessary to develop an electronic cigarette that has the taste of the real cigarette to fill the gap in the market.

CONTENTS OF INVENTION

The technical problem to be solved by the present invention is to provide an electronic cigarette atomizer in view of the shortcomings of the prior art so as to improve the smoking taste and solve the problems that the burnt flavor is produced easily and that tobacco tar leaks in an atomization process by using heating wires.

In order to solve the above technical problem, the technical solution adopted by the present invention is as follows: an electronic cigarette atomizer includes a shell; one end of the shell is in fixed connection with a suction nozzle; an ultrasonic atomization piece is fixed in the shell; the ultrasonic atomization piece is in contact with a liquid guide body; the liquid guide body is communicated with a liquid storage cavity; a smoke output surface of the ultrasonic atomization piece is communicated with an airflow passage; solid perfume and a heating device which heats the solid perfume are provided in the airflow passage (the solid perfume can be set to be in contact with the heating device); the airflow passage is communicated with the suction nozzle; and the ultrasonic atomization piece is a solid piezoelectric ceramic atomization piece.

By means of the above structure, when the electronic cigarette atomizer works, the tobacco tar is atomized to form smoke by the ultrasonic atomization piece, at the same time, the heating device starts to heat the solid perfume in the airflow passage, so that the solid perfume produce fragrance, finally the smoke and the fragrance are mixed, therefore the mixed smoke has fragrance or real cigarette fragrance and is inhaled by users, and accordingly the demand of the users for the taste of real cigarette is satisfied.

Further, the cavity of the shell forms the liquid storage cavity; a vent pipe is provided in the liquid storage cavity; an upper end of the vent pipe is communicated with the suction nozzle; a lower end of the vent pipe is in fixed connection with an upper fixing base; one end, away from the vent pipe, of the upper fixing base is fixed in a lower fixing base; the lower fixing base is in fixed connection with one end, away from the suction nozzle, of the shell; the ultrasonic atomization piece is provided in the lower fixing base below the vent pipe, and the ultrasonic atomization piece, the upper fixing base and the lower end of the vent pipe are enclosed to form an atomization cavity; the surface, close to the vent pipe, of the ultrasonic atomization piece is in contact with the liquid guide body; one end, away from the suction nozzle, of the lower fixing base and the ultrasonic atomization piece are enclosed to form a hollow cavity, and a vent groove is provided in an inner wall of a side edge of the lower fixing base; and the vent groove communicates the atomization cavity with the hollow cavity.

The vent pipe penetrates through the liquid storage cavity until it reaches the smoke output surface of the ultrasonic atomization piece, the vent groove is provided in the inner wall of the side edge of the lower fixing base for communicating the atomization cavity with the hollow cavity, and when the electronic cigarette atomizer works, the airflow passes by the hollow cavity, the vent groove and the atomization cavity so as to take the smoke produced by ultrasonic atomization to the suction nozzle from the airflow passage to be inhaled by the users and to prevent the smoke from accumulating in the atomization cavity to affect the taste of the smoke during the next inhalation; meanwhile, a part of the heat produced by the ultrasonic atomization piece at work disperses to the air in the hollow cavity, when the airflow passes by the hollow cavity, the airflow takes away the heat and the smoke produced by ultrasonic atomization, thereby the phenomenon that the ultrasonic atomization piece is damaged due to high temperature can be reduced, meanwhile the phenomenon that the smoke is condensed in the airflow passage can also be reduced.

Further, the liquid guide body includes a main body, and a projection which stretches into the liquid storage cavity is provided on the main body; and the main body is in contact with the projection, and the main body is in contact with the surface close to the vent pipe of the ultrasonic atomization piece.

A preferred embodiment of the liquid guide body structure is adopted, the shape and the size of the main body are matched with the size of the outer diameter of the ultrasonic atomization piece or are smaller than the outer diameter of the ultrasonic atomization piece, the main body is a circular bottom, and at least one projection is provided on the circular bottom; and the projection stretches into the liquid storage cavity after penetrating through a through hole in the upper fixing base. It is ensured that the tobacco tar in the liquid storage cavity can be timely supplied to the ultrasonic atomization piece for working, and the main body of the liquid guide body can also be propped on the surface of the ultrasonic atomization piece to prevent that the atomization effect is affected because the main body of the liquid guide body is not in contact with the ultrasonic atomization piece from.

Further, a top end of the shell and the bottom of the suction nozzle are hermetically connected by a sealing ring so as to prevent tobacco tar leakage of the atomizer, facilitate the detachment of the suction nozzle and guarantee good sanitation and hygiene.

Further, a bottom end of the lower fixing base is in fixed connection with a connecting base; a connecting electrode is fixed in the connecting base; an air inlet passage is provided in the connecting electrode; the air inlet passage is communicated with an inner cavity of the lower fixing base; and the air inlet passage, the hollow cavity, the vent groove, the atomization cavity and the vent pipe are communicated with each other in sequence to form the airflow passage.

As a preferred embodiment, a perfume sleeve which stores the solid perfume is fixed between the vent pipe and the suction nozzle; a first vent hole is formed in the upper end of the perfume sleeve; the heating device is fixed in the perfume sleeve; the lower end of the perfume sleeve is in insulation connection with a first electrode, and the upper end of the first electrode which stretches into the perfume sleeve is provided with a second vent hole; one electrode of the heating device is electrically connected with the first electrode, and the other electrode of the heating device is electrically connected with the perfume sleeve; and the vent pipe is communicated with the suction nozzle through the second vent hole and the first vent hole in sequence. After the smoke produced by the oscillation of the ultrasonic atomization piece passing by the vent pipe, the smoke is mixed with the fragrance which is produced by heating the solid perfume by heating device, and finally enters the suction nozzle to be inhaled by the users so as to improve the user's experience of the smoke, for example, the smoke taste and mouth feel of real cigarette are simulated.

Further, the first electrode is in contact with a second electrode; the second electrode is in insulation connection with the sealing ring; and the top end of the vent pipe is provided in the sealing ring. While the structure stability and the convenient detachment of the perfume sleeve are facilitated to change or add perfume, good electrical contact is also guaranteed.

As another preferred embodiment, the solid perfume is filled in the hollow cavity below the ultrasonic atomization piece and is in contact with a lower surface of the ultrasonic atomization piece. Therefore, the heat produced by the ultrasonic atomization piece at work is transferred to the solid perfume, and more uniform heating of the solid perfume can also be guaranteed under the oscillation of the solid perfume so as to make full use of the heat produced by the ultrasonic atomization piece.

Further, the heating device is fixed in the hollow cavity and is in contact with the solid perfume, and the hollow cavity is located between the ultrasonic atomization piece and the connecting electrode.

By means of the above structure, both the heating device and the ultrasonic atomization piece heat the solid perfume, so that the heating of the solid perfume is more uniform, the heating speed is higher, and the produced fragrance is more uniform.

Further, the heating device is a ceramic heating piece, a heating wire and other materials with heating or heat transfer properties.

Further, a tobacco tar injection hole is provided in the sealing ring; and the tobacco tar injection hole is sealed by a tobacco tar injection plug. Thus, tobacco tar can be injected conveniently.

Compared with the prior art, the present invention has the following beneficial effects: the present invention adopts the ultrasonic atomization piece to atomize the tobacco tar to produce smoke, meanwhile the solid perfume are heated by the heating device to produce the fragrance, finally the smoke is fixed with the fragrance, in this case, the mixed smoke has the fragrance of the real cigarette, thereby improving the smoking taste, and the structure is relatively simple; in an ultrasonic atomization process of the tobacco tar, the sealing property is good, the ultrasonic atomization power is relatively small, and the problems that the burnt flavor is produced easily and that the tobacco tar leaks in the atomization process of the heating wire are solved; and the smoking taste is improved, the solid perfume can be changed or added conveniently, the use cost is reduced and the electronic cigarette atomizer is easier to implement and popularize.

SPECIFIC MODE FOR CARRYING OUT THE INVENTION

Such words expressing orientations as "upper end", "lower end", "top end", "tail end", "bottom end" and the like mentioned in the present invention are based on the reference that the electronic cigarette atomizer of the present invention is vertically or perpendicularly placed on a horizontal plane (i.e., the electronic cigarette atomizer forms an angle of 90 degrees with the horizontal plane), and the suction nozzle is upward.

Figure 1:
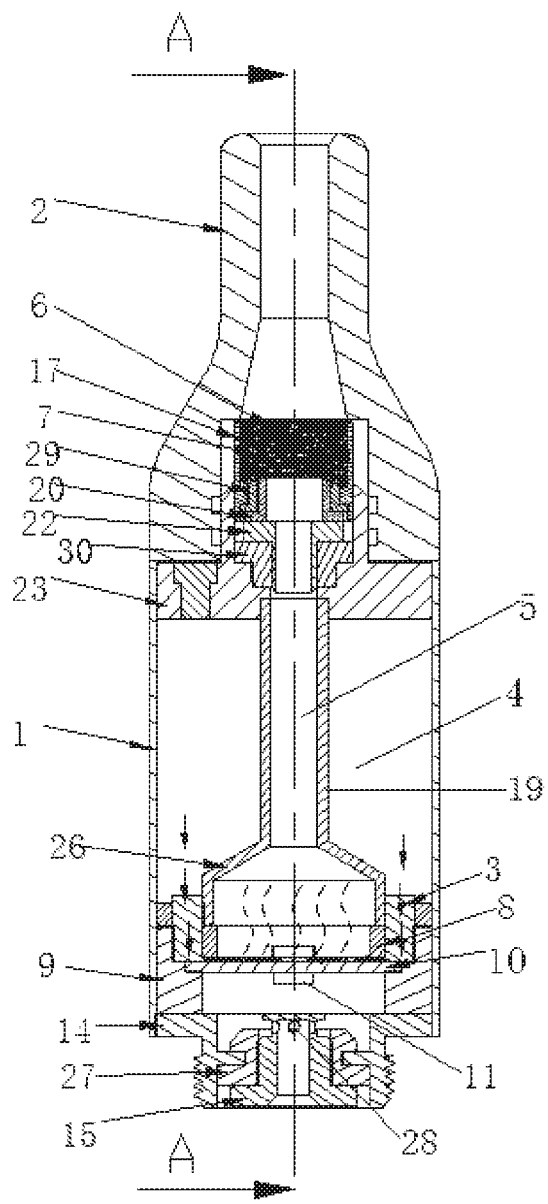
FIG. 1 is a sectional view of embodiment 1 of the present invention.
Figure 2:
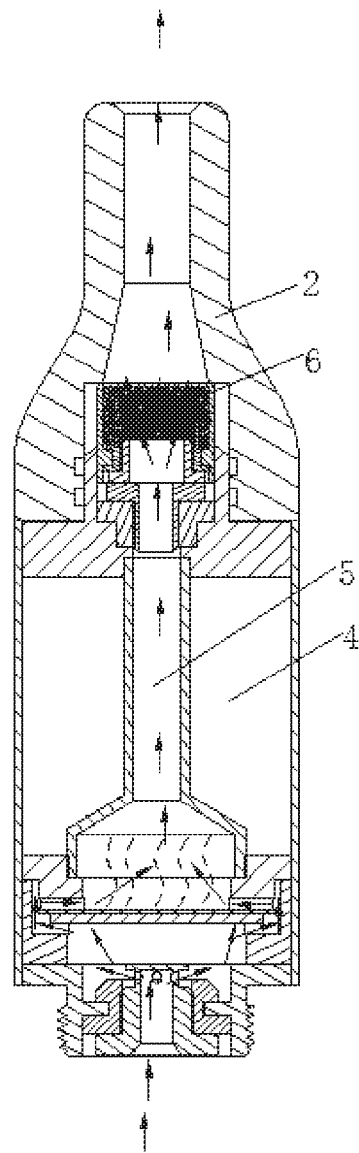
FIG. 2 is a sectional view of an A-A surface of FIG. 1.

As shown in FIG. 1 and FIG. 2, embodiment 1 of the present invention includes a shell 1; a sealing ring 23 is provided in an upper end of the shell 1, a projection is provided on the sealing ring 23, and a suction nozzle 2 is connected with a shell 1 by means of a plug connection of the projection and the suction nozzle 2; an ultrasonic atomization piece 10 is fixed in a lower end of the shell 1; a liquid guide body 3 is provided on a upper end face of the ultrasonic atomization piece 10 and is in contact with the end face; the liquid guide body 3 is communicated with a liquid storage cavity 4; an atomization outlet of the ultrasonic atomization piece 10 is communicated with a bottom end of an airflow passage 5; a cavity for accommodating solid perfume 6 and a heating device 7 is provided in the sealing ring 23 so as to conveniently replace the solid perfume 6 and the heating device 7; meanwhile, the airflow passage 5 penetrates through the solid perfume 6 and the heating device 7; the solid perfume 6 are in contact with the heating device 7 which supplies heat to the solid perfume 6; and a tail end (i.e., one end of a smoke outflow direction) of the airflow passage 5 is communicated with the suction nozzle 2.

Figure 3:
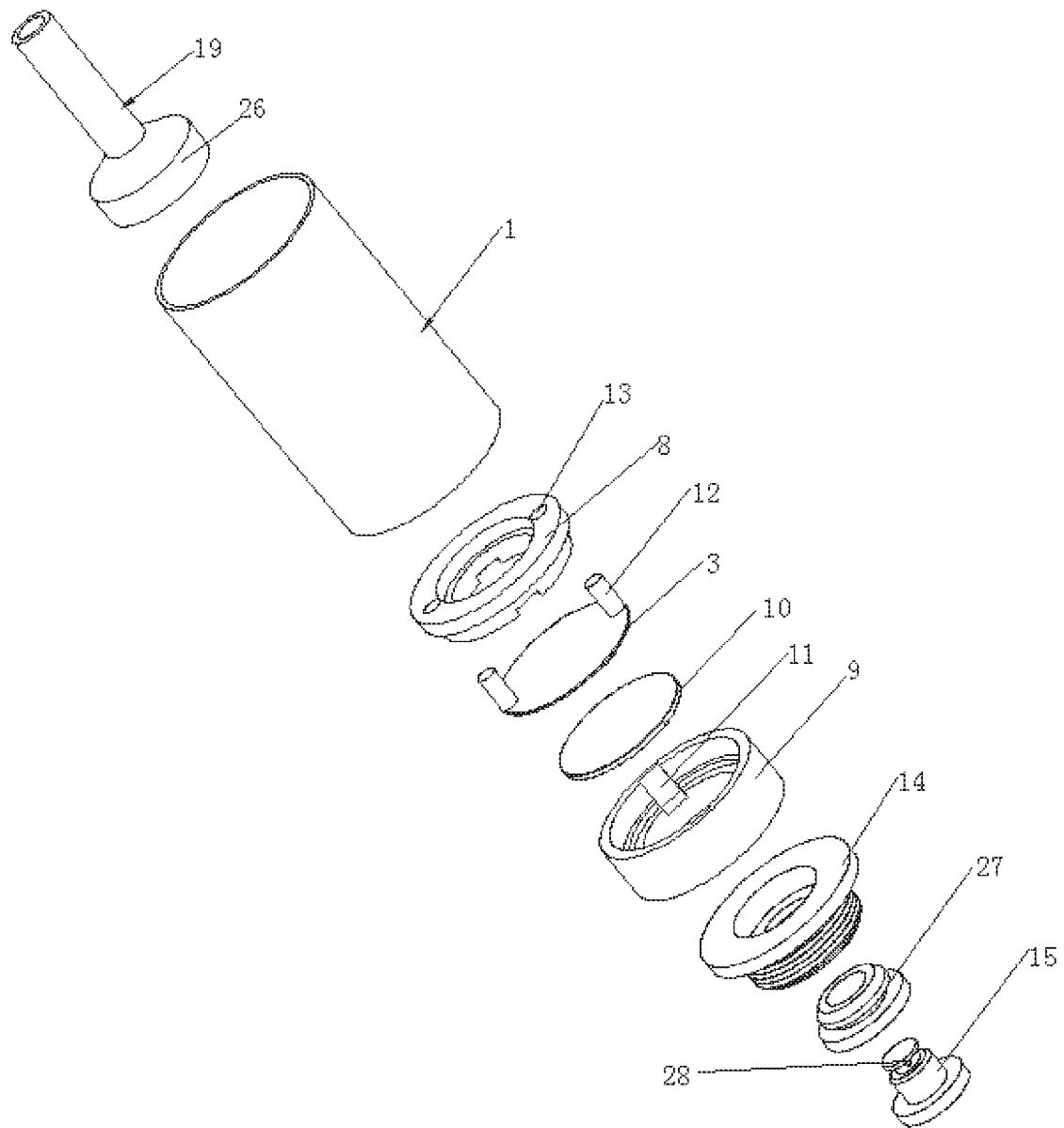
FIG. 3 is a structural explosive view between a vent pipe and a connecting base in embodiment 1 of the present invention.

As shown in FIG. 1 and FIG. 3, the cavity in the shell 1 forms the liquid storage cavity 4; a vent pipe 19 is provided in the liquid storage cavity 4; the upper end of the vent pipe 19 is inserted into the sealing ring 23 and is in tensioning fit with the sealing ring 23, and the airflow passage 5 penetrates through the interior of the vent pipe 19 to be communicated with the suction nozzle 2; the lower end of the vent pipe 19 is of horn-shaped structure, and the horn-shaped structure is covered on a fixing base 8 and is in tensioning fit and fixed connection with the fixing base 8; one end, away from the vent pipe 19, of the upper fixing base 8 is clamped and fixed in a lower fixing base 9; the lower fixing base 9 is in buckled connection or threaded connection with one end, away from the suction nozzle 2, of the shell 1; the ultrasonic atomization piece 10 is provided in the lower fixing base 9 below the vent pipe 19, and the surface of the ultrasonic atomization piece 10 which is close to the vent pipe 19 is in contact with the liquid guide body 3; the ultrasonic atomization piece 10, the upper fixing base 8 and the horn-shaped structure on the lower end of the vent pipe 19 are enclosed to form an atomization cavity; the ultrasonic atomization piece 10 atomizes the tobacco tar conveyed by the liquid guide body 3 in the atomization cavity; a vent groove 11 is provided in an inner wall of a side edge of the lower fixing base 9; the ultrasonic atomization piece 10 and the lower fixing base 9 are enclosed to form a hollow cavity;

and the vent groove 11 communicates the atomization cavity with the hollow cavity, so that the airflow flows by the surface of the liquid guide body 3 which is deviated from the ultrasonic atomization piece 10 and takes away the smoke atomized by the ultrasonic atomization piece 10.

As shown in FIG. 3, the liquid guide body 3 includes a main body, and a projection 12 which stretches into the liquid storage cavity 4 is provided on the main body; the shape and the size of the main body are matched with the size of the outer diameter of the ultrasonic atomization piece 10 or are smaller than the outer diameter of the ultrasonic atomization piece 10, the main body is a circular bottom, and at least one projection 12 (in the present invention, two projections are provided on the circular bottom, and the positions of the two projections are opposite to each other, so that the inner structure of the atomizer is more stable) is provided on the circular bottom; and the projection 12 stretches into the liquid storage cavity 4 after penetrating through a through hole 13 in the upper fixing base 8.

As shown in FIG. 3, the upper fixing base 8, the lower fixing base 9 and a connecting base 14 are all provided with hollow structures penetrating through the two ends; the upper surface (the surface close to the suction nozzle 2) of the bottom of the liquid guide body 3 is communicated with the hollow structure of the upper fixing base 8, and the hollow structure of the upper fixing base 8 is communicated with the vent pipe 19, namely, the main body of the liquid guide body 3 is provided in the atomization cavity and is in contact with the surface of the ultrasonic atomization piece. For the convenience of installation, a mounting boss 26 is provided on the bottom end (the lower end of the horn-shaped structure) of the vent pipe 19, the outside diameter of the mounting boss 26 is matched with the inside diameter of the upper fixing base 8, and the mounting boss 26 can be in fixed connection with the upper fixing base 8 in a threaded connection so as to facilitate the installation and the detachment.

A bottom end of the lower fixing base 9 is in fixed connection with the connecting base 14; a connecting electrode 15 is fixed in the connecting base 14; an air inlet passage 16 penetrating through the connecting electrode 15 is provided in the connecting electrode 15; the lower fixing base 9, the connecting base 14 and the ultrasonic atomization piece 10 are enclosed to form a hollow cavity, and the air inlet passage 16 is communicated with the lower hollow cavity; and the air inlet passage 16, the hollow cavity, the vent groove 11, the atomization cavity and the vent pipe 19 are communicated with each other in sequence to form the airflow passage 5.

A top end of the connecting electrode 15 stretches into the hollow cavity inside the lower fixing base 9, the connecting electrode 15 and the connecting base 14 are insulated by a first insulating ring 27, a plurality of vent holes 28 are provided in a side wall of the top end of the connecting electrode 15, the vent holes 28 are communicated with the air inlet passage 16 in the connecting electrode 15, and the vent holes 28 can cause the airflow to disperse toward all the directions so as to prevent the airflow from being blocked.

Figure 4:
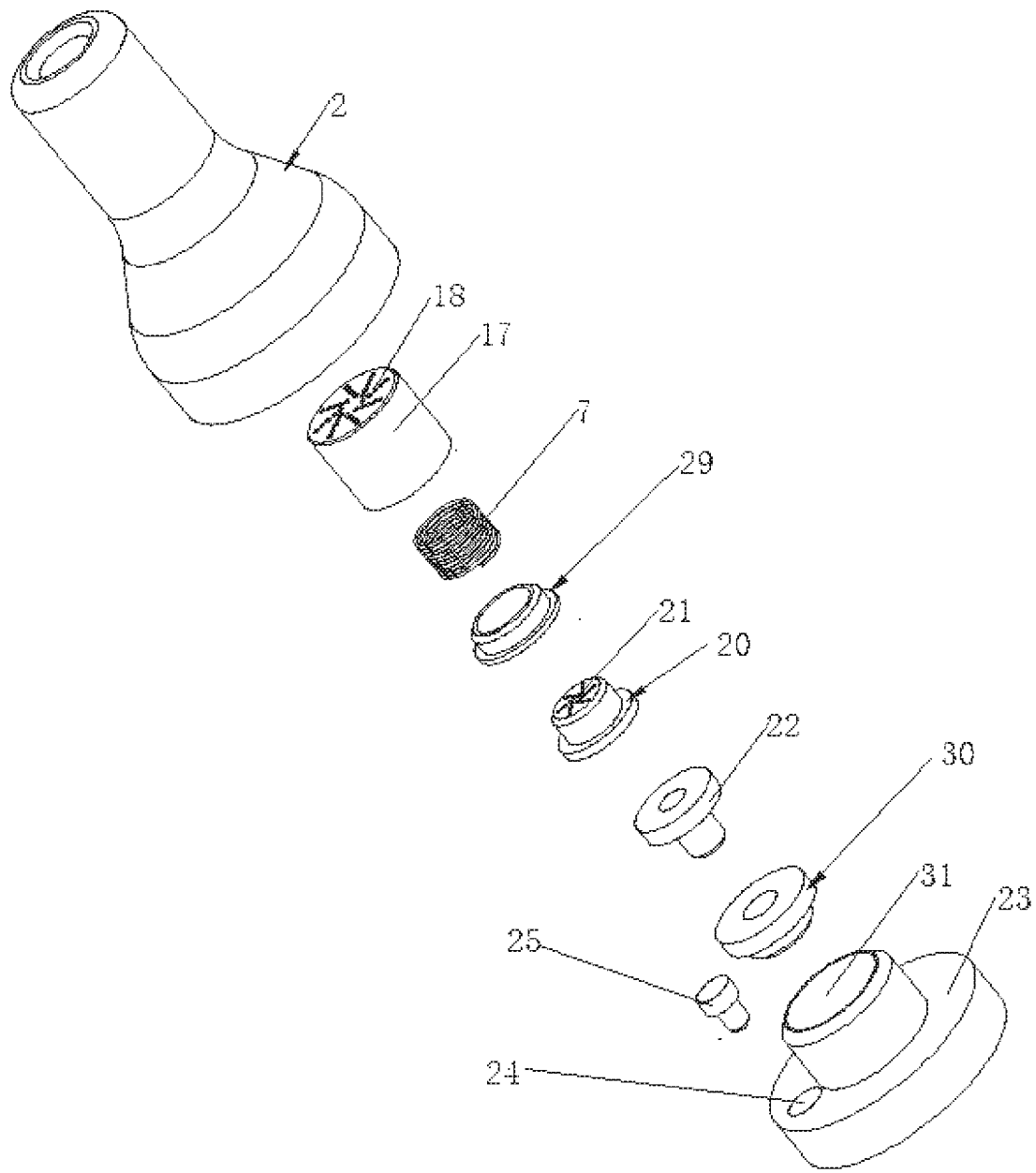
FIG. 4 is a structural explosive view between a suction nozzle and an insulating ring in embodiment 1 of the present invention.
Figure 5:
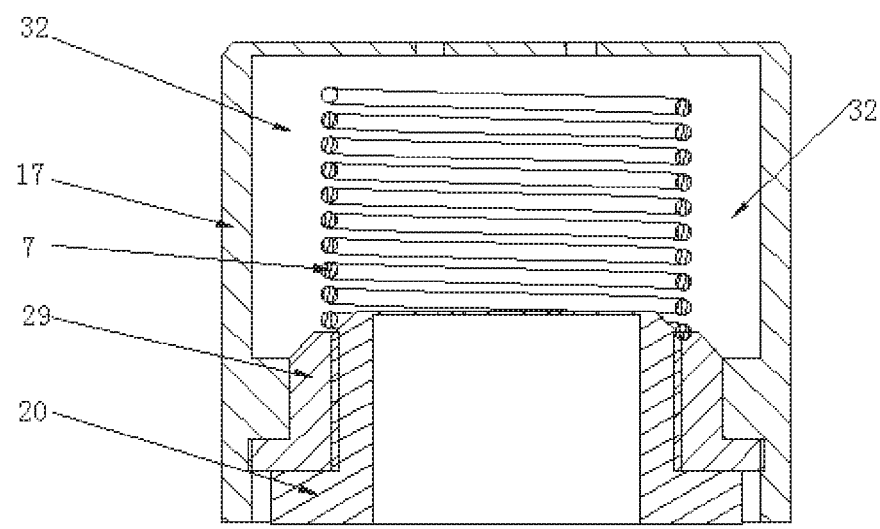
FIG. 5 is a structural view of an inner structure of a perfume sleeve in embodiment 1 of the present invention.

As shown in FIG. 4 and FIG. 5, a perfume sleeve 17 with an open lower end is fixed in the cavity in the projection of the sealing ring 23; the solid perfume are provided in the perfume sleeve 17, and a first vent hole 18 is provided in the upper end of the perfume sleeve 17; the heating device 7 is fixed in the perfume sleeve 17 and is in contact with the solid perfume; the lower end of the perfume sleeve 17 is in insulation connection with a first electrode 20, and the upper end of the first electrode 20 which stretches into the perfume sleeve 17 is provided with a second vent hole 21, the smoke enters the inner cavity of the perfume sleeve 17 from the second vent hole 21 through the vent pipe 19 to be mixed with the fragrance which is produced by heating the solid perfume, and the mixed smoke is exhausted from the first vent hole 18 to be inhaled by the users; one electrode of the heating device 7 is in contact with the first electrode 20, and the other electrode of the heating device is in contact with the perfume sleeve 17 so as to realize electrical connection; and the first electrode 20 is in insulation connection with the perfume sleeve 17 through a second insulating ring 29 so as to prevent short circuit.

As shown in FIG. 5, the heating device 7 can be a heating wire, the heating wire is fixed in the inner cavity 32 of the perfume sleeve 17, the solid perfume are filled in the inner cavity 32 of the perfume sleeve 17 and are in contact with the heating wire, so that the solid perfume are heated by the heating wire to release fragrance.

The first electrode 20 is in contact with a second electrode 22; the second electrode 22 is in insulation connection with the sealing ring 23; and the top end of the vent pipe 19 is provided in the sealing ring 23.

As shown in FIG. 1 and FIG. 4, the top end of the shell 1 is hermetically and detachably connected with the bottom of the suction nozzle 2 through the sealing ring 23, a mounting hole 31 (i.e., a cavity) is provided in the end face close to the suction nozzle of the sealing ring 23, and one end, provided with the second electrode 22, of the perfume sleeve 17 is fixed in the mounting hole 31; and after the suction nozzle is detached, the perfume sleeve 17 can be detached to replace the solid perfume.

As shown in FIG. 4, the bottom end of the second electrode 22 stretches into the middle hollow cavity of a third insulating ring 30, and an outer wall of the third insulating ring 30 is in interference connection with the inner wall of the mounting hole 31.

Figure 6:
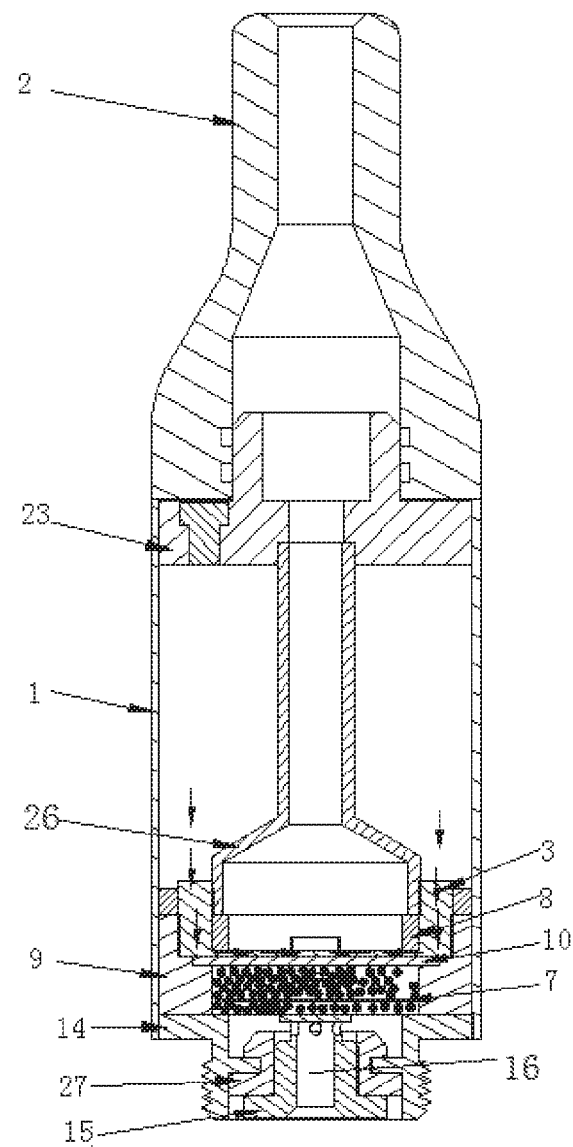
FIG. 6 is a sectional view of embodiment 2 of the present invention.
Figure 7:
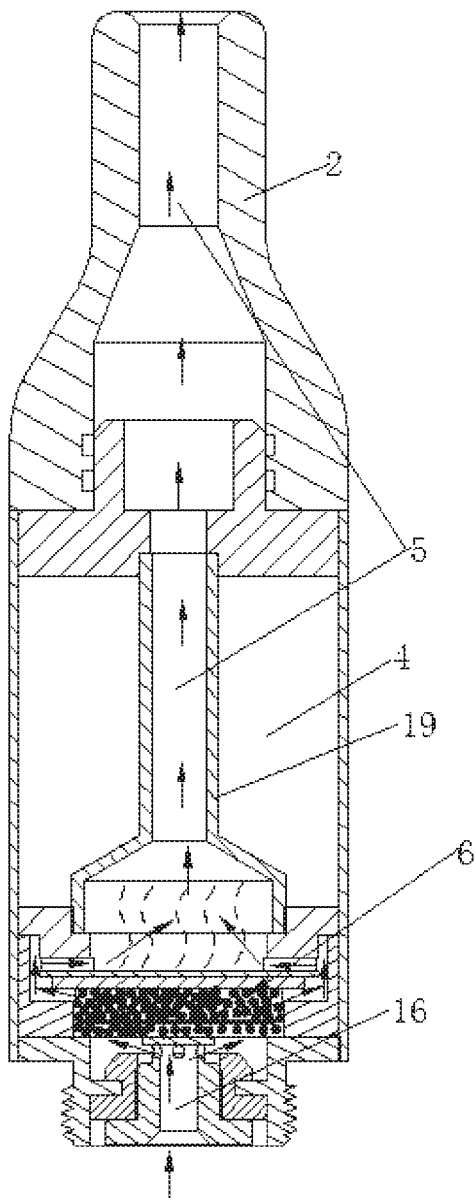
FIG. 7 is a schematic diagram of an airflow direction of embodiment 2 of the present invention.

As shown in FIG. 6 and FIG. 7, the solid perfume 6 in embodiment 2 of the present invention are filled in the lower fixing base 8 (i.e., the hollow cavity) below the ultrasonic atomization piece 10, and the surface, away from the vent pipe 19, of the ultrasonic atomization piece 10 is in contact with the solid perfume 6. As the solid perfume are in contact with the surface of the ultrasonic atomization piece, in an oscillation process of the ultrasonic atomization piece, the solid perfume can be stirred to a certain extent, so that the solid perfume are heated more uniformly; and the solid perfume can also be heated to release the fragrance.

The heating device 7 is a heating piece fixed in the solid perfume 6, so that both the heating piece and the ultrasonic atomization piece 10 heat the solid perfume 6, and accordingly, the solid perfume 6 are heated more uniformly and it can quickly release the fragrance to be inhaled by the user; and an air pass hole is provided in the heating piece, when the airflow enters from the air inlet passage 16, the airflow enters a perfume-filled cavity (i.e., the hollow cavity) to bring the fragrance of the solid perfume into the vent pipe 19 so as to be mixed with the smoke atomized by the ultrasonic atomization piece, and the mixed smoke is inhaled by the user.

The ultrasonic atomization piece 10 is a solid piezoelectric ceramic piece.

In the present invention, for the convenience of tobacco tar injection, a tobacco tar injection hole 24 is provided in the sealing ring 23; and the tobacco tar injection hole 24 is sealed by a tobacco tar injection plug 25.

The invention claimed is:

1. An electronic cigarette atomizer, comprising a shell; wherein:
   one end of the shell is in fixed connection with a suction nozzle, and an ultrasonic atomization piece is fixed in the shell;
   the ultrasonic atomization piece is in contact with a liquid guide body;
   the liquid guide body is fluidly communicated with a liquid storage cavity;
   a smoke output surface of the ultrasonic atomization piece is fluidly communicated with an airflow passage;
   solid perfume and a heating device which heats the solid perfume are provided in the airflow passage;
   the airflow passage is fluidly communicated with the suction nozzle;
   wherein a cavity of the shell forms the liquid storage cavity;
   a vent pipe is provided in the liquid storage cavity;
   an upper end of the vent pipe is communicated with the suction nozzle;
   a lower end of the vent pipe is in fixed connection with an upper fixing base;
   one end, away from the vent pipe, of the upper fixing base is fixed in a lower fixing base;
   the lower fixing base is in fixed connection with one end, away from the suction nozzle, of the shell;
   the ultrasonic atomization piece is provided in the lower fixing base below the vent pipe, and
   the ultrasonic atomization piece, the upper fixing base and the lower end of the vent pipe are enclosed to form an atomization cavity;
   a surface, close to the vent pipe, of the ultrasonic atomization piece is in contact with the liquid guide body;
   one end, away from the suction nozzle, of the lower fixing base and the ultrasonic atomization piece are enclosed to form a hollow cavity, and
   a vent groove is provided in an inner wall of a side edge of the lower fixing base; and
   the vent groove fluidly communicates the atomization cavity with the hollow cavity.

2. The electronic cigarette atomizer of claim 1, wherein the ultrasonic atomization piece is a solid piezoelectric ceramic atomization piece.

3. The electronic cigarette atomizer of claim 1, wherein:
   the liquid guide body comprises a main body;
   a projection which stretches into the liquid storage cavity is provided on the main body, and
   the main body is in contact with the ultrasonic atomization piece; and
   the main body is in contact with the surface, close to the vent pipe, of the ultrasonic atomization piece.

4. The electronic cigarette atomizer of claim 1, wherein a top end of the shell and the bottom of the suction nozzle are hermetically connected by a sealing ring.

5. The electronic cigarette atomizer of claim 4, wherein:
   a bottom end of the lower fixing base is in fixed connection with a connecting base;
   a connecting electrode is fixed in the connecting base; an air inlet passage is provided in the connecting electrode;
   the air inlet passage is fluidly communicated with a hollow cavity of the lower fixing base; and
   the air inlet passage, the hollow cavity, the vent groove, the atomization cavity and the vent pipe are fluidly communicated with each other in sequence to form the airflow passage.

6. The electronic cigarette atomizer of claim 5, wherein:
   a perfume sleeve which stores the solid perfume is fixed between the vent pipe and the suction nozzle;
   a first vent hole is formed in an upper end of the perfume sleeve;
   the heating device is fixed in the perfume sleeve;
   a lower end of the perfume sleeve is in insulation connection with a first electrode, and
   the upper end of the first electrode which stretches into the perfume sleeve is provided with a second vent hole; and
   the vent pipe is fluidly communicated with the suction nozzle-through the second vent hole and the first vent hole in sequence.

7. The electronic cigarette atomizer of claim 6, wherein:
   the first electrode is in contact with a second electrode;
   the second electrode is in insulation connection with the sealing ring; and
   the top end of the vent pipe is provided in the sealing ring.

8. The electronic cigarette atomizer of claim 4, wherein the solid perfume is filled in a hollow cavity of the lower fixing base below the ultrasonic atomization piece and is in contact with a lower surface of the ultrasonic atomization piece.

9. The electronic cigarette atomizer of claim 8, wherein the heating device is fixed in the cavity of the lower fixing base below the ultrasonic atomization piece and is in contact with the solid perfume.

10. The electronic cigarette atomizer of claim 4, wherein a tobacco tar injection hole is provided in the sealing ring; and the tobacco tar injection hole is sealed by a tobacco tar injection plug.

11. The electronic cigarette atomizer of claim 5, wherein a tobacco tar injection hole is provided in the sealing ring; and the tobacco tar injection hole is sealed by a tobacco tar injection plug.

12. The electronic cigarette atomizer of claim 6, wherein a tobacco tar injection hole is provided in the sealing ring; and the tobacco tar injection hole is sealed by a tobacco tar injection plug.

13. The electronic cigarette atomizer of claim 7, wherein a tobacco tar injection hole is provided in the sealing ring; and the tobacco tar injection hole is sealed by a tobacco tar injection plug.

14. The electronic cigarette atomizer of claim 8, wherein a tobacco tar injection hole is provided in the sealing ring; and the tobacco tar injection hole is sealed by a tobacco tar injection plug.

15. The electronic cigarette atomizer of claim 9, wherein a tobacco tar injection hole is provided in the sealing ring; and the tobacco tar injection hole is sealed by a tobacco tar injection plug.

\* \* \* \* \*